(12) United States Patent
Sandstrom

(10) Patent No.: US 10,758,349 B2
(45) Date of Patent: *Sep. 1, 2020

(54) DELIVERY DEVICE FOR PROSTHETIC HEART VALVE WITH CAPSULE ADJUSTMENT DEVICE

(71) Applicant: Medtronic Vascular, Inc., Santa Rosa, CA (US)

(72) Inventor: Jeffrey Sandstrom, Scandia, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 536 days.

This patent is subject to a terminal disclaimer.

(21) Appl. No.: 14/656,838

(22) Filed: Mar. 13, 2015

(65) Prior Publication Data

US 2016/0262883 A1   Sep. 15, 2016

(51) Int. Cl.
  *A61F 2/24*    (2006.01)
  *A61F 2/95*    (2013.01)
  *A61F 2/962*   (2013.01)

(52) U.S. Cl.
  CPC ............. *A61F 2/2436* (2013.01); *A61F 2/95* (2013.01); *A61F 2/2427* (2013.01); *A61F 2/962* (2013.01); *A61F 2002/9517* (2013.01)

(58) Field of Classification Search
  CPC .. A61F 2/2436; A61F 2002/9517; A61F 2/95; A61F 2/2427; A61F 2/962
  See application file for complete search history.

(56) References Cited

U.S. PATENT DOCUMENTS 5,433,723 A * 7/1995 Lindenberg ............... A61F 2/88
                                                    606/198
5,707,376 A * 1/1998 Kavteladze ............... A61F 2/90
                                                    623/1.11

(Continued)

FOREIGN PATENT DOCUMENTS

CN       103655004      3/2014
EP        0990426       4/2000
(Continued)

OTHER PUBLICATIONS

PCT/US2017/021709, The International Search Report and The Written Opinion of the International Searching Authority, dated May 24, 2017.

(Continued)

*Primary Examiner* — Jing Rui Ou

(57) ABSTRACT

A delivery device for percutaneously delivering a stented prosthetic heart includes a sheath, a handle, and adjustment device including a fine adjustment mechanism, and an outer stability shaft. The sheath defines a lumen and is configured to compressively constrain the stented prosthetic heart valve. The handle is coupled to the proximal portion of the sheath and includes an actuator mechanism coupled to a proximal portion of the sheath that is configured to selectively move the sheath relative to the housing to release the stented prosthetic heat valve. The adjustment device is coupled to the handle and includes an adjustment lumen through which the sheath and the handle slidably extend. The outer stability shaft is coupled to the adjustment device. The fine adjustment mechanism is configured to selectively move the handle and the sheath relative to the adjustment device and the outer stability shaft.

13 Claims, 10 Drawing Sheets

(56) References Cited

U.S. PATENT DOCUMENTS

| | | | | |
|---|---|---|---|---|
| 7,105,016 B2* | 9/2006 | Shiu | | A61F 2/95 604/523 |
| 7,662,186 B2 | 2/2010 | Bagga et al. | | |
| 7,740,655 B2 | 6/2010 | Birdsall | | |
| 7,824,443 B2* | 11/2010 | Salahieh | | A61F 2/2418 623/2.11 |
| 7,976,574 B2* | 7/2011 | Papp | | A61F 2/95 623/1.11 |
| 8,465,541 B2 | 6/2013 | Dwork | | |
| 8,491,650 B2 | 7/2013 | Wiemeyer et al. | | |
| 8,579,963 B2 | 11/2013 | Tabor | | |
| 8,585,750 B2* | 11/2013 | Argentine | | A61F 2/95 623/1.12 |
| 9,050,067 B2* | 6/2015 | Duncan | | A61B 17/0057 |
| 9,095,465 B2* | 8/2015 | Kelly | | A61F 2/966 |
| 9,724,223 B2* | 8/2017 | Dooley | | A61F 2/95 |
| 2002/0103525 A1* | 8/2002 | Cummings | | A61F 2/95 623/1.11 |
| 2003/0191516 A1* | 10/2003 | Weldon | | A61F 2/95 623/1.12 |
| 2003/0212411 A1* | 11/2003 | Jansen | | A61M 25/0113 606/108 |
| 2004/0006380 A1* | 1/2004 | Buck | | A61F 2/966 623/1.11 |
| 2004/0148009 A1* | 7/2004 | Buzzard | | A61F 2/95 623/1.12 |
| 2004/0153137 A1* | 8/2004 | Gaschino | | A61F 2/95 623/1.11 |
| 2005/0060016 A1* | 3/2005 | Wu | | A61F 2/95 623/1.11 |
| 2005/0080476 A1* | 4/2005 | Gunderson | | A61F 2/95 623/1.11 |
| 2007/0156225 A1* | 7/2007 | George | | A61F 2/95 623/1.12 |
| 2007/0191865 A1* | 8/2007 | Pappas | | A61F 2/966 606/108 |
| 2008/0188920 A1* | 8/2008 | Moberg | | A61F 2/95 623/1.12 |
| 2009/0192584 A1* | 7/2009 | Gerdts | | A61F 2/95 623/1.11 |
| 2009/0254165 A1* | 10/2009 | Tabor | | A61F 2/2439 623/1.11 |
| 2010/0312332 A1* | 12/2010 | Forster | | A61F 2/2418 623/2.1 |
| 2011/0224774 A1* | 9/2011 | Silveira | | A61F 2/962 623/1.11 |
| 2011/0251679 A1 | 10/2011 | Wiemeyer et al. | | |
| 2011/0251683 A1 | 10/2011 | Tabor | | |
| 2011/0257733 A1 | 10/2011 | Dwork | | |
| 2011/0264199 A1 | 10/2011 | Tran et al. | | |
| 2011/0282425 A1 | 11/2011 | Dwork | | |
| 2012/0053574 A1 | 3/2012 | Murray, III et al. | | |
| 2012/0185031 A1 | 7/2012 | Ryan et al. | | |
| 2012/0310332 A1 | 12/2012 | Murray et al. | | |
| 2013/0013047 A1* | 1/2013 | Ramos | | A61F 2/966 623/1.11 |
| 2013/0274856 A1 | 10/2013 | Arbefeuille et al. | | |
| 2014/0135909 A1 | 5/2014 | Carr et al. | | |
| 2015/0223955 A1 | 8/2015 | Li et al. | | |
| 2015/0305902 A1* | 10/2015 | Argentine | | A61F 2/966 623/1.12 |

FOREIGN PATENT DOCUMENTS

| | | |
|---|---|---|
| WO | WO2009/137359 | 11/2009 |
| WO | WO2012/116368 | 8/2012 |
| WO | WO20120116368 A2 | 8/2012 |
| WO | WO2016/149083 | 9/2016 |

OTHER PUBLICATIONS

PCT/US2016/020275, The International Search Report and The Written Opinion of the International Searching Authority, dated Jun. 15, 2016.

CN Office Action communication dated Dec. 3, 2018 in corresponding Chinese Appln. No. 201680015278.3 (English translation).

* cited by examiner

DELIVERY DEVICE FOR PROSTHETIC HEART VALVE WITH CAPSULE ADJUSTMENT DEVICE

FIELD OF THE INVENTION

The present invention relates to systems and methods for percutaneous implantation of a prosthetic heart valve. More particularly, it relates to the systems and methods for the fine adjustment and placement of a stented prosthetic heart valve via transcatheter implantation.

BACKGROUND

Heart valves are sometimes damaged by disease or by aging, resulting in problems with the proper functioning of the valve. Heart valve replacement has become a routine surgical procedure for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a valve prosthesis is compacted for delivery in a catheter and then advanced, for example through an opening in the femoral artery, and through the descending aorta to the heart, where the prosthesis is then deployed in the valve annulus (e.g., the aortic valve annulus).

Various types and configurations of prosthetic heart valves are available for percutaneous valve replacement procedures. In general, prosthetic heart valve designs attempt to replicate the function of the valve being replaced and thus will include valve leaflet-like structures. Valve prostheses are generally formed by attaching a bioprosthetic valve to a frame made of a wire or a network of wires. Such a valve prosthesis can be contracted radially to introduce the valve prosthesis into the body of the patient percutaneously through a catheter. The valve prosthesis can be deployed by radially expanding it once positioned at the desired target site.

In addition to the delivery device itself, typical transcatheter heart implantation techniques entail the use of a separate introducer device to establish a portal to the patient's vasculature (e.g., femoral artery) and through which the prosthetic valve-loaded delivery device is inserted. The introducer device generally includes a relatively short sheath and a valve structure. By inserting the prosthetic heart valve-loaded sheath through the introducer valve and sheath, a low friction hemostasis seal is created around the outer surface of the delivery sheath. While highly desirable, friction between the introducer device and the delivery sheath can be problematic, leading to unexpected movement of the prosthesis prior to release from the delivery device. If the deployed prosthesis is incorrectly positioned relative to the native annulus, serious complication may arise including paravalvular leakage (PVL) or the requirement for placement of a permanent pacemaker.

For example, FIG. 1A illustrates, in simplified form, an introducer device 10 establishing a portal to a patient's vasculature 12, and through which a prosthetic heart valve-loaded delivery shaft 14 has been inserted. As shown, delivery shaft 14 has been manipulated to locate the loaded prosthetic heart valve 16 (generally referenced) near a desired position relative to an aortic valve 18. An outer delivery sheath 20 contains the prosthetic heart valve 16. However, it is not always possible to accurately position the delivery device containing the prosthetic heart valve 16 at the desired position. Accordingly, adjustments in the position must be made. Conventionally, adjusting the position of the prosthetic heart valve 16 is accomplished by moving handle 22 proximally or distally. In the example of FIG. 1B, handle 22 is moved proximally. However, as handle 22 is moved proximally, outer delivery sheath 20 pulls towards the inner wall of the descending aorta 29 and away from outer wall of aortic arch 28. With this movement, handle 22 has moved, but prosthetic heart valve 16 has not moved relative to aortic valve 18. Thus, it takes more movement of handle 22 to move prosthetic heart valve 22. Further, the location of prosthetic heart valve 16 often needs to be adjusted a very small amount, which is difficult to accomplish by pushing or pulling handle 22.

Accordingly, there is a need for an improved adjustment mechanism and method to more accurately position a prosthetic heart valve implanted via transcatheter delivery devices and methods.

SUMMARY OF THE INVENTION

Embodiments hereof relate to a delivery device for percutaneously delivering a stented prosthetic heart valve to the site of a damaged or diseased native valve. The stented prosthetic heart valve is radially expandable from a radially compressed configuration to a radially expanded configuration. The delivery device includes a sheath, a handle, and adjustment device including a fine adjustment mechanism, and an outer stability shaft. The sheath defines a lumen and is configured to compressively constrain the stented prosthetic heart valve. The handle is coupled to the proximal portion of the sheath and includes an actuator mechanism coupled to a proximal portion of the sheath that is configured to selectively move the sheath relative to the housing to release the stented prosthetic heat valve. The adjustment device is coupled to the handle and includes an adjustment lumen through which the sheath and the handle slidably extend. The outer stability shaft is coupled to the adjustment device. The fine adjustment mechanism is configured to selectively move the handle and the sheath relative to the adjustment device and the outer stability shaft.

Embodiments hereof also relate to a method for restoring a defective heart valve in a patient. The method includes manipulating a delivery device to guide a prosthetic heart valve through a patient's vasculature and into the defective heart valve by moving a handle of the delivery device. The delivery device is loaded with a prosthetic heart valve in a radially compressed configuration, the prosthetic heart including a stent frame to which a valve structure is attached. The delivery device includes a delivery sheath, an outer stability shaft, a handle, and an adjustment device. The sheath constrains the prosthetic heart valve in the radially compressed configuration. The outer stability shaft is coaxially received over the delivery sheath and terminates proximal of the prosthetic heart valve when the delivery device is in the delivery configuration. The handle includes a housing and an actuating mechanism coupled to the delivery sheath.

The adjustment device is coupled to the handle. Moving the handle causes the adjustment device, delivery sheath, and the outer stability shaft to move. The location of the prosthetic heart valve within the defective heart valve is finely adjusted by manipulating the fine adjustment mechanism of the adjustment device. Manipulating the fine adjustment mechanism causes the handle and the delivery sheath to move relative to the adjustment device and the outer stability shaft. The delivery sheath is withdrawn from the prosthetic heart valve by actuating the actuator mechanism such that the delivery sheath slides relative to the outer stability shaft and the handle to release the prosthetic heart valve from the delivery sheath. With the release of the prosthetic heart valve from the delivery sheath, the prosthetic heart valve self-expands into engagement with the native heart valve.

DETAILED DESCRIPTION

Specific embodiments of the present invention are now described with reference to the figures, wherein like reference numbers indicate identical or functionally similar elements. The terms "distal" and "proximal", when used in the following description to refer to a catheter or delivery device, are with respect to a position or direction relative to the treating clinician. Thus, "distal" and "distally" refer to positions distant from, or in a direction away from, the clinician and "proximal" and "proximally" refer to positions near, or in a direction toward, the clinician.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

As referred to herein, the stented prosthetic heart valves used in accordance with and/or as part of the various systems, devices, and methods of the present disclosure may include a wide variety of different configurations, such as a bioprosthetic heart valve having tissue leaflets or a synthetic heart valve having polymeric, metallic, or tissue-engineered leaflets, and can be specifically configured for replacing any heart valve.

In general terms, the stented prosthetic heart valve of the present disclosure includes a stent supporting a valve structure (tissue or synthetic), with the stent having a normal, expanded configuration that is collapsible to a compressed configuration for loading within a delivery device. The stent is usually constructed to self-deploy or expand when released from the delivery device. For example, the stented prosthetic heart valve useful with the present disclosure can be a prosthetic heart valve sold under the trade name CoreValve® available from Medtronic CoreValve, LLC. Other non-limiting examples of the transcatheter heart valve prostheses useful with the systems, devices, and methods of the present disclosure are described in U.S. Pat. Nos. 7,662,186; and 7,740,655, which are incorporated in their entirety by reference herein. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured.

Figure 2A:
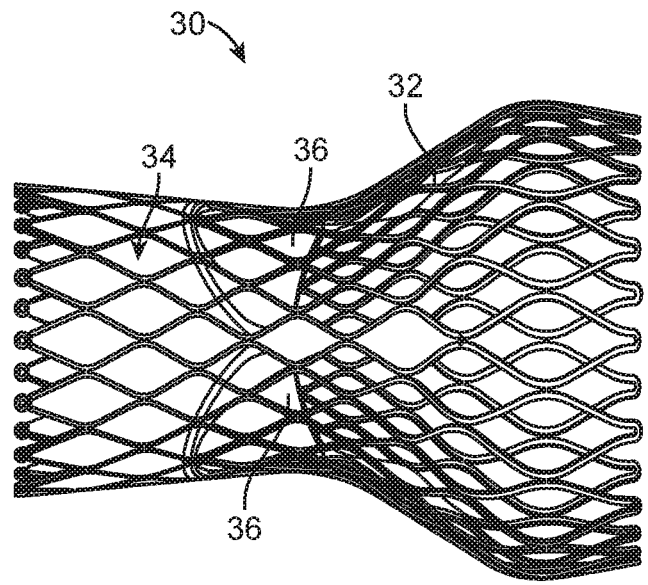
FIG. 2A is a side illustration of a stented prosthetic heart valve useful with systems, devices, and methods of the present disclosure and in a normal, expanded configuration.
Figure 2B:
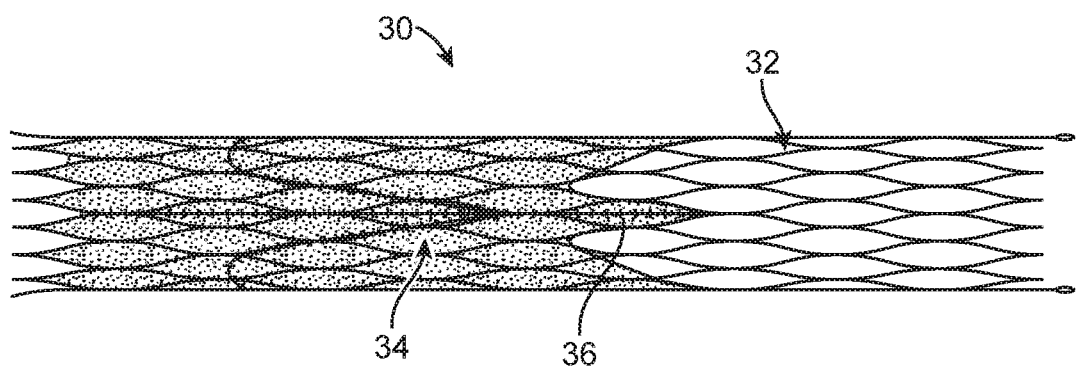
FIG. 2B is a side illustration of the prosthetic heart valve of FIG. 2A in a radially compressed configuration.

With the above understanding in mind, one non-limiting example of a stented prosthetic heart valve 30 useful with systems, devices, and methods of the present disclosure is illustrated in FIG. 2A. As a point of reference, the prosthetic heart valve 30 is shown in a normal, pre-set, or expanded configuration in the view of FIG. 2A. FIG. 2B illustrates the prosthetic heart valve 30 in a compressed configuration (e.g., when compressively retained within an outer catheter or sheath). Prosthetic heart valve 30 includes a stent, or stent frame 32, and a valve structure 34. The valve structure 34 is assembled to stent frame 32 and provides two or more (typically three) leaflets 36. Stent frame 32 may assume differing forms and construction based upon application needs as described in greater detail in U.S. Pat. No. 8,579,963, which is incorporated in its entirety by reference herein.

Figure 3:
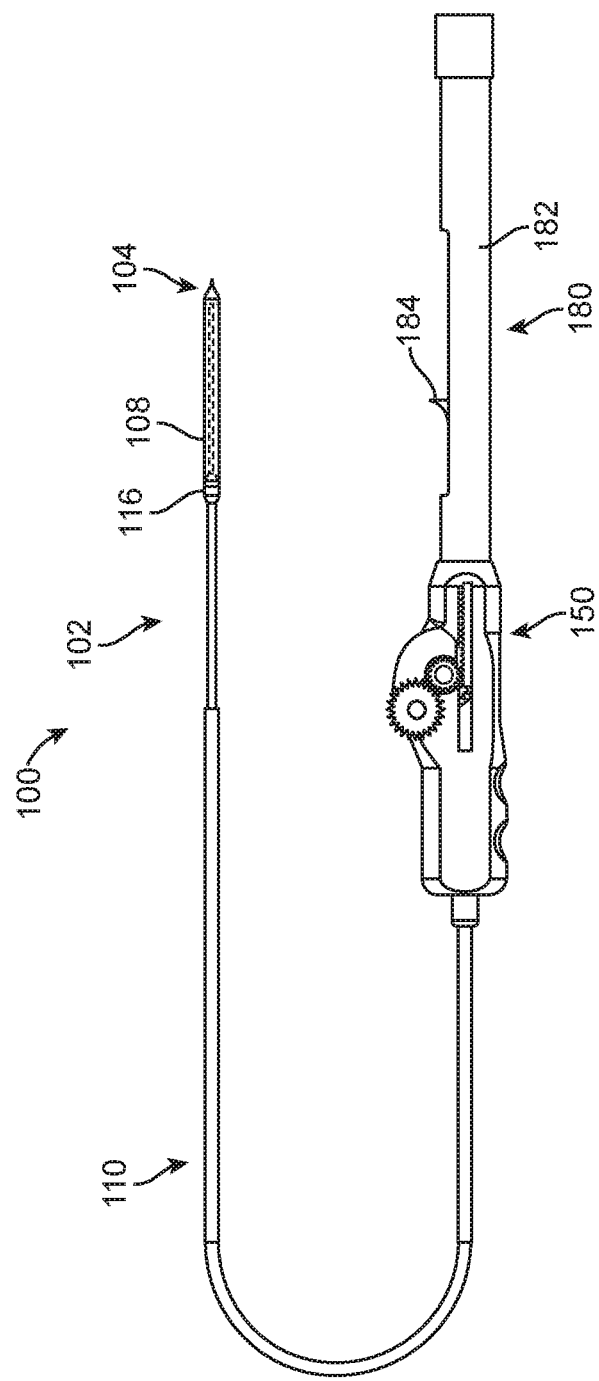
FIG. 3 is a side illustration of the delivery device of the present disclosure.

With the above understanding of the stented prosthetic heart valve 30 in mind, one embodiment of a delivery device 100, in accordance with the present disclosure, for percutaneously delivering and implanting a prosthetic heart valve 30, is shown in FIG. 3. Delivery device 100 may assume differing forms and construction based upon application needs as described in greater detail in U.S. Pat. Nos. 8,579,963; 8,491,650; and 8,465,541, which are incorporated in their entirety by reference herein.

Delivery device 100 includes a handle 180, an adjustment device 150, an outer stability shaft 110, a delivery sheath assembly 102, and an inner shaft assembly 104 as shown in FIG. 3. Each of these components is described in greater detail below. Delivery device 100 is configured to be used for transcatheter valve implantation. Other embodiments of the delivery device and adjustment device are possible. Delivery device 100, described in greater detail below, is merely an exemplary embodiment of a transcatheter delivery device and modifications can be made to the embodiments described herein without departing from the spirit and scope of the present invention. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

Figure 4:
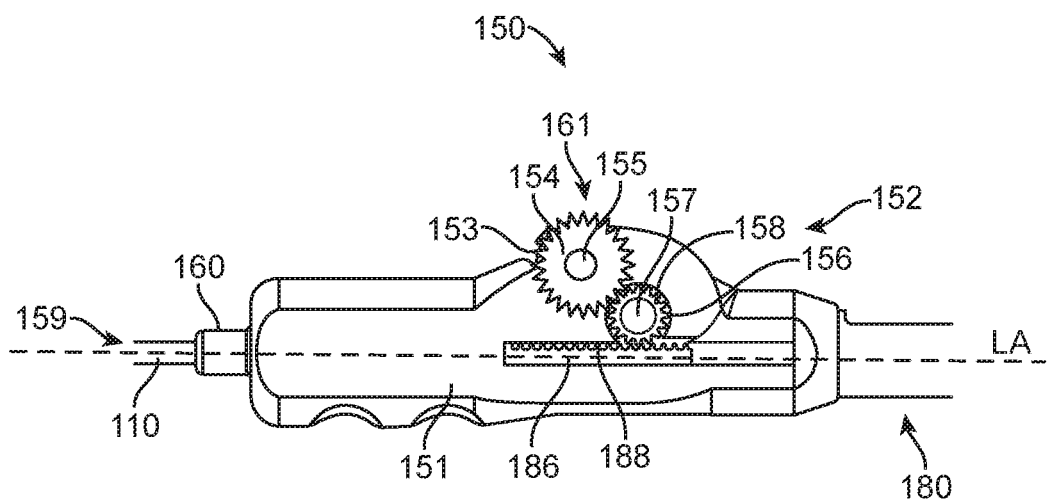
FIG. 4 is a cutaway illustration of an adjustment device of the delivery device of FIG. 3.
Figure 5:
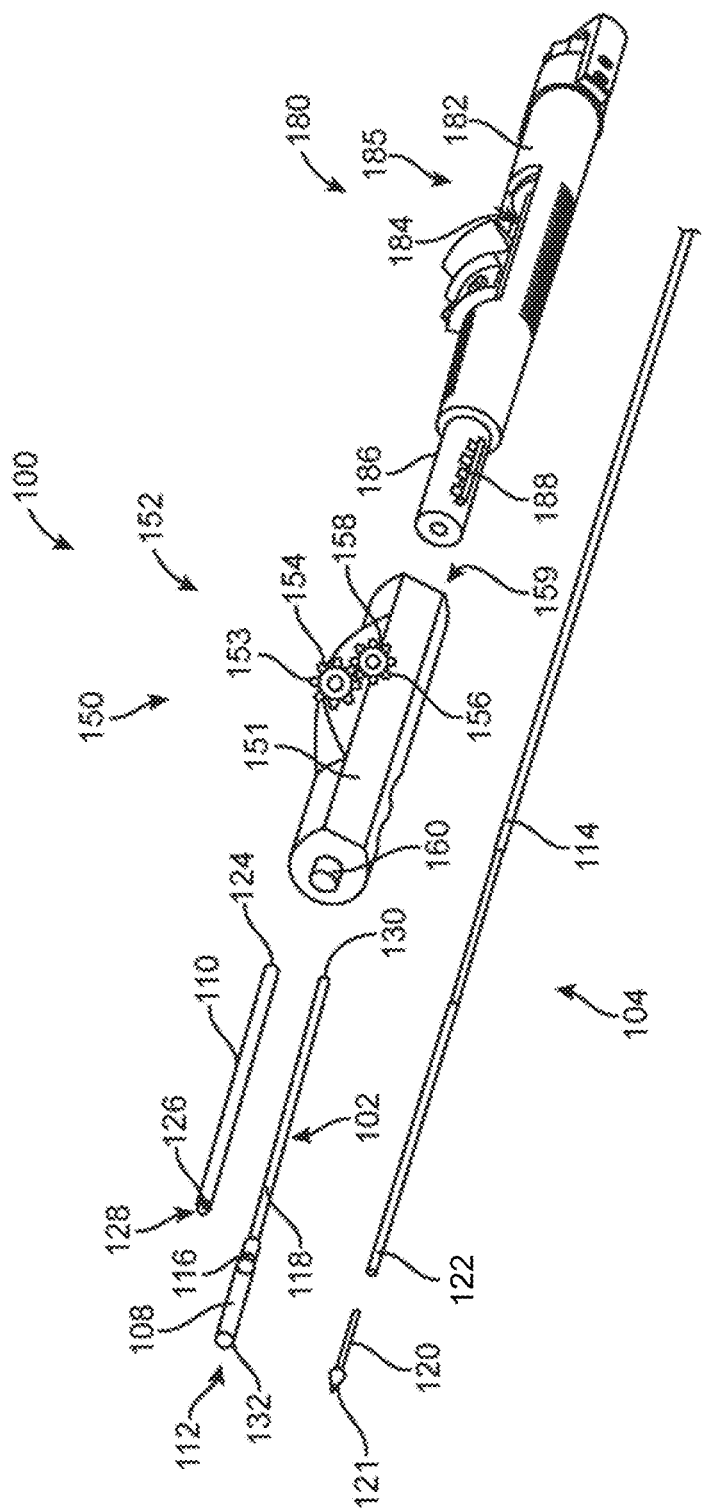
FIG. 5 is an exploded perspective illustration of the delivery device of FIG. 3.
Figure 6:
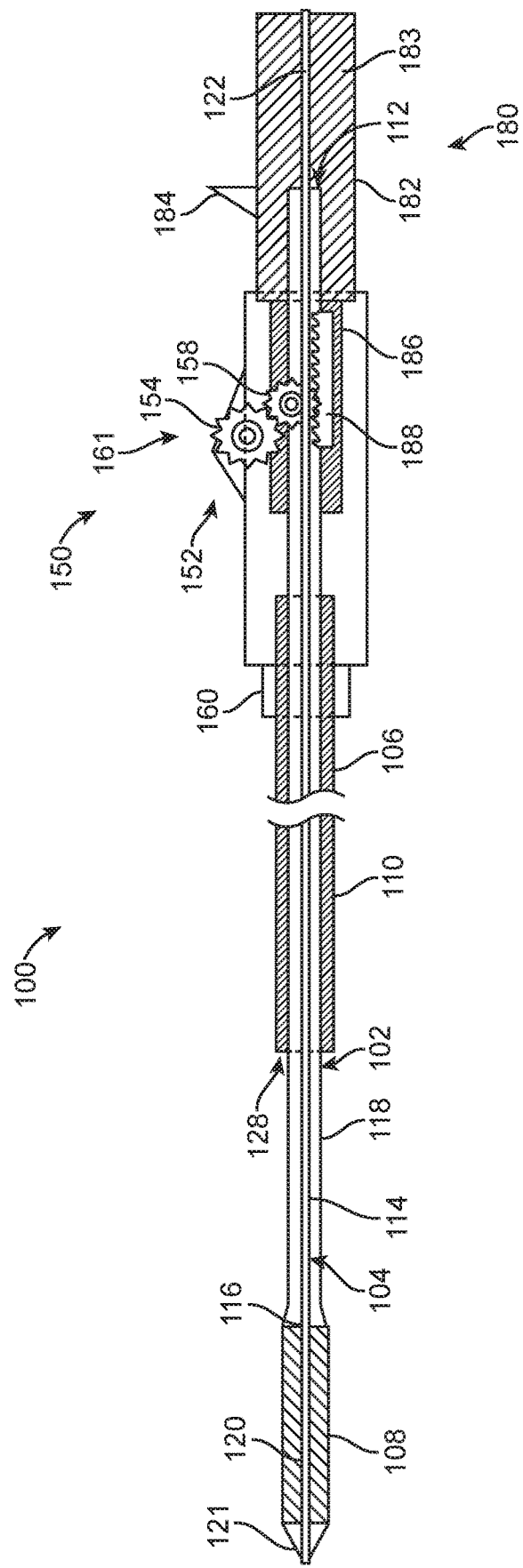
FIG. 6 is a cutaway illustration of the delivery device of FIG. 3.
Figure 7A:
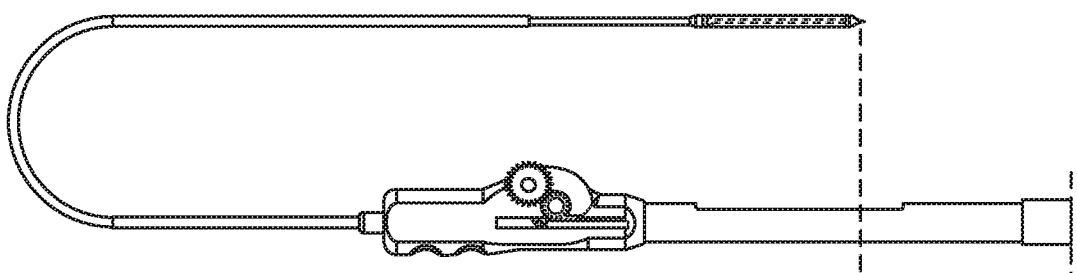
FIGS. 7A-7E are illustrations of the adjustment of the location of a capsule of the delivery device of FIG. 3.
Figure 7B:
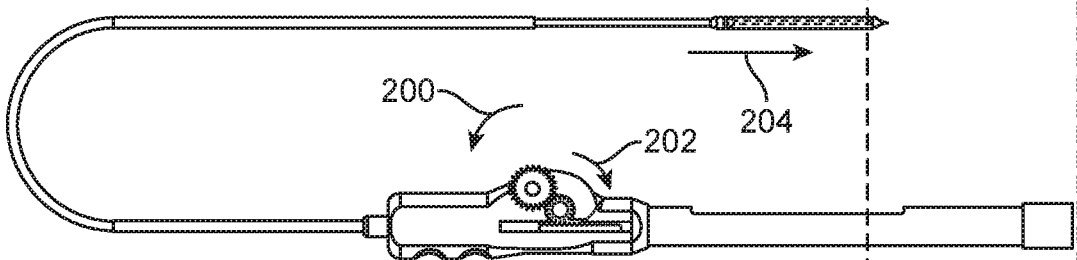
Figure 7C:
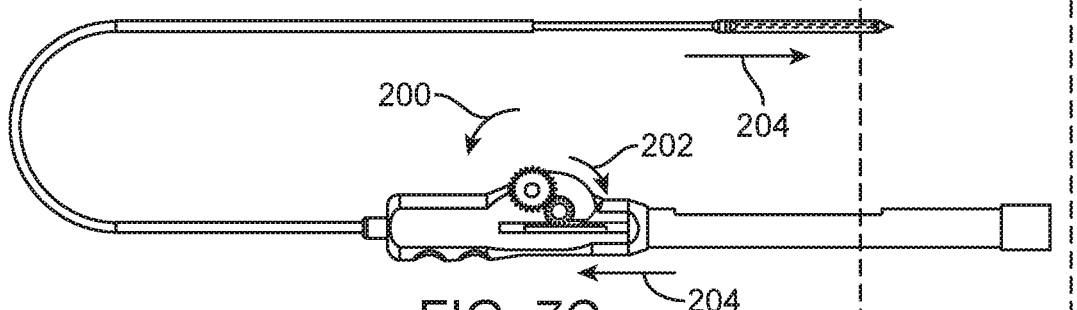
Figure 7D:
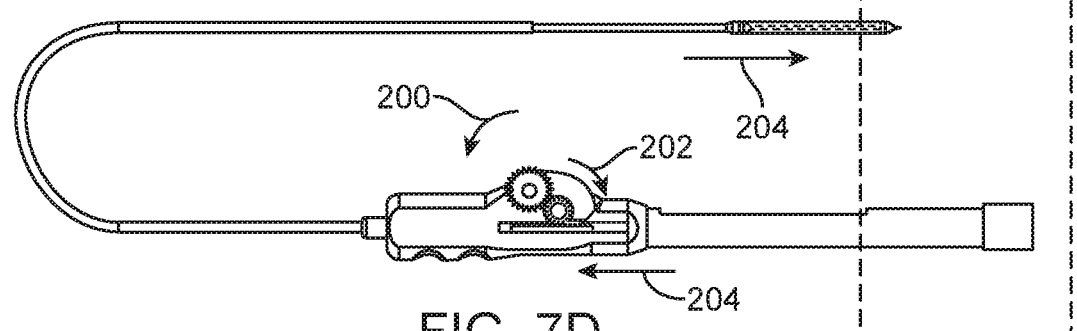
Figure 7E:
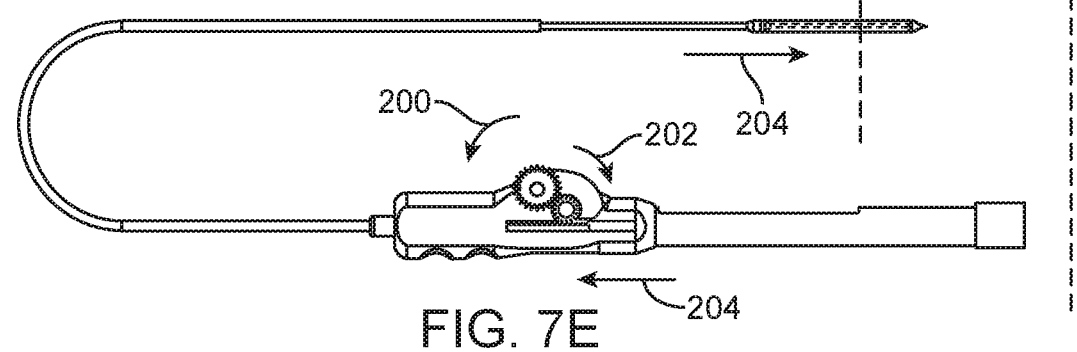

Components in accordance with the embodiment of delivery device 100 of FIG. 3 are presented in greater detail in FIGS. 4-6. Various features of the components of delivery device 100 reflected in FIGS. 4-6 and described below can be modified or replaced with differing structures and/or mechanisms. The present disclosure is in no way limited to delivery sheath assembly 102, inner shaft assembly 104, outer stability shaft 110, adjustment device 150, and handle 180 shown and described below. In more general terms, delivery devices in accordance with the principles of the present disclosure provide features capable of compressively retaining a self-expanding, stented prosthetic heart valve (e.g., the capsule 108), along with an mechanism and method for finely adjusting the position of a self-expanding, stented prosthetic heart valve (e.g., adjustment device 150) within a defective heart valve.

In the embodiment of FIGS. 4-6, delivery sheath assembly or sheath 102 includes a capsule 108 and a shaft 118, and defines a lumen 112 extending from a proximal end 130 to a distal end 132 of delivery sheath assembly 102. The length and thickness of capsule 108 are determined by the requirements of the specific application and are described in greater detail in U.S. Pat. No. 8,579,963, previously incorporated by reference herein. Shaft 118 is configured for fixed connection to capsule 108 at connection point 116, and extends proximally from capsule 108, with shaft 118 configured for fixed connection of delivery sheath assembly 102 to handle 180. Although delivery sheath assembly 102 is described herein as including capsule 108 and shaft 118, capsule 108 may simply be an extension of shaft 118 and the delivery sheath assembly 102 may be described simply as sheath 102. An outer diameter of capsule 108 is greater than an outer diameter of proximal shaft 118.

Inner shaft assembly 104 can assume a variety of configurations described in greater detail in U.S. Pat. No. 8,579,963, previously incorporated by reference herein. In general, inner shaft assembly 104 includes a proximal inner shaft 114, a retention member 120, and a tip 121. Proximal inner shaft 114 connects to retention member 120, and retention member 120 connects to tip 121. Proximal inner shaft 114 is configured for fixed connection of inner shaft assembly 104 to handle 180. The components of inner shaft assembly 104 combine to define a continuous lumen 122, which is sized to receive an auxiliary component such as a guide wire (not shown). Although inner shaft assembly 104 is described herein as including proximal inner shaft 114, retention member 120, and tip 121, retention member 120 and tip 121 may simply be an extension of proximal inner shaft 114 and the inner shaft assembly 104 may be described simply as inner shaft 104.

Outer stability shaft 110 can assume a variety of configurations described in greater detail in U.S. Pat. No. 8,579,963, previously incorporated by reference herein. In general, outer stability shaft 110 is configured for fixed connection to adjustment device 150. Outer stability shaft 110 serves as a stability shaft for delivery device 100, and has a proximal end 124, a distal end 126, and a passageway 128 extending between ends 124 and 126. The passageway is sized to coaxially receive delivery sheath assembly 102, and in particular shaft 118, in a manner permitting the sliding of shaft 118 relative to outer stability shaft 110. In an example, in a delivery configuration, connection point 116 is distal of distal end 126 of outer stability shaft 110 by a distance in the range of 3-13 cm. Further, in a deployed configuration, connection point 116 is distal of distal end 126 of stability shaft 110.

Handle 180 can assume a variety of configurations described in greater detail in U.S. Pat. No. 8,579,963, previously incorporated by reference, and modified herein. In general, handle 180 includes a housing 182, an actuator mechanism 184, a handle extension 186, and teeth 188 on handle extension 186. Housing 182 retains actuator mechanism 184. Sheath 102 is coupled to actuator mechanism 184 such that movement of actuator mechanism 182 causes sheath 102 to move relative to outer stability shaft 110 and inner shaft assembly 104, as described below. Handle extension 186 extends from the distal end of housing 182.

In the embodiment of FIGS. 5-6, handle 180 provides a surface for convenient handling and grasping by a user, and can have a generally cylindrical shape as shown. While the handle of FIGS. 5-6 is shown with a cylindrical shape, it is not meant to limit the design, and other shapes and sizes are contemplated based on application requirements.

Handle 180 is configured to maintain portions of the actuator mechanism 184 within a cavity 183 defined by housing 182. In the embodiment shown in FIGS. 5-6, housing 180 further forms a longitudinal slot 185 through which actuator mechanism 184 extends for interfacing by a user. Handle extension 186 extends distally from housing 182 and provides a mounting surface for teeth 188. For example, and not by way of limitation, teeth 188 may be formed integrally as part of handle extension 186 or may be coupled to handle extension 186 by adhesives, welding, clamping, and other coupling devices as appropriate. While FIGS. 5-6 show teeth 188 located on one side of handle extension 186, this is not meant to limit the design, and teeth 188 may be located elsewhere on handle extension 186.

Adjustment device 150, as shown in the embodiment of FIGS. 4-6, includes an adjustment housing 151, an adjustment mechanism 152, and an extension 160 at the distal end of adjustment device 150. The components of adjustment device 150 combine to define a continuous lumen 159 through adjustment device 150. The proximal portion of lumen 159 is configured to accept handle extension 186 of handle 180. A distal portion of lumen 159 defined by extension 160 is configured to accept the proximal end of outer stability shaft 110. Outer stability shaft 110 may be coupled to extension 160 by adhesives, welding, clamping, and other coupling devices, as appropriate.

Adjustment device 150 provides a surface for convenient handling and grasping by a user, and can have a generally cylindrical shape as shown. While adjustment device 150 of FIGS. 4-6 is shown with a cylindrical shape, it is not meant to limit the design, and other shapes and sizes are contemplated based on application requirements. Adjustment device 150 is configured to maintain portions of adjustment mechanism 152 within a cavity defined by housing 151. In the embodiment shown in FIG. 5, housing 151 further includes a longitudinal slot 161 through which adjustment mechanism 152 extends for interfacing by a user.

Adjustment mechanism 152 includes a first toothed wheel 154 and a second toothed wheel 158, as shown in FIGS. 4-6. First toothed wheel 154 has teeth 153. Second toothed wheel 158 has teeth 156. First toothed wheel 154 is disposed within housing 151 on a first pivot axis 155 such that first toothed wheel 154 rotates about first pivot axis 155. The upper radius of first toothed wheel 154 extends through longitudinal slot 161 in housing 151 for user interface. Second toothed wheel 158 is disposed within housing 151 on a second pivot axis 157 such that second toothed wheel 158 rotates about second pivot axis 157. Teeth 156 on second toothed wheel 158 are configured to engage with teeth 188 on handle extension 186, as described in more detail below. First toothed wheel 154 and second toothed wheel 158 are configured such that teeth 153 of first toothed wheel 154 engage with teeth 156 of second toothed wheel 158. While FIGS. 4-6 show adjustment mechanism 152 having a specific number of teeth 153 on first toothed wheel 154 and a specific number of teeth 156 on second toothed wheel 158, this is not meant to limit the design and the number of teeth 153 and 156 may assume other configurations.

Adjustment mechanism 152 is generally constructed to provide selective retraction/advancement of handle 180, delivery sheath assembly 102, and inner shaft assembly 104 relative to housing 151 of adjustment device 150 and outer stability shaft 110. Adjustment mechanism 152 can have a variety of constructions and/or devices capable of providing the desired user interface and the current embodiment shown in FIGS. 4-6 is not meant to limit the design, but rather provide an example of one possible embodiment. For example, other embodiments of adjustment device 152 may utilize only first toothed wheel 152 to engage teeth 188 on handle extension 186.

When delivery device 100 is assembled, handle extension 186 resides within the proximal portion of lumen 159 of adjustment device 150, and is configured such that teeth 188 on handle extension 186 engage teeth 156 of second toothed wheel 158 of adjustment device 150. Handle extension 186 is sized such that it may fit within lumen 159 of adjustment device 150 and retract/advance within lumen 159 with user actuation of adjustment mechanism 152 of adjustment device 150.

Actuator mechanism 184 is generally constructed to provide selective retraction/advancement of the delivery sheath assembly 102 and can have a variety of constructions and/or devices capable of providing the desired user interface. One example of an actuator mechanism 184 is further described in U.S. Pat. No. 8,579,963, previously incorporated by reference herein.

Construction of delivery device 100 is reflected in FIGS. 5-6 and includes delivery sheath assembly 102 being coaxially and slidably disposed between inner shaft assembly 104 and outer stability shaft 110. FIG. 6 shows delivery device 100 in the delivery configuration, with a prosthetic heart valve in a radially compressed configuration loaded within capsule 108. As shown in FIG. 6, capsule 108 is coaxially disposed over retention member 120 of inner shaft assembly 104. Inner shaft assembly 104 is rigidly connected to housing 182. Delivery sheath assembly 102 is movably connected to housing 182 via actuator mechanism 184. Outer stability shaft 110 is rigidly connected to adjustment device 150, as described previously. Generally speaking, delivery sheath assembly 102 can be retracted in a proximal direction relative to inner shaft assembly 104, outer stability shaft 110, and housing 182 from the delivery configuration of FIG. 6 to a deployed configuration wherein capsule 108 is retracted proximally such that capsule 108 does not surround the prosthetic heart valve. This allows the prosthetic heart valve to radially expand for engagement with the native heart valve (not shown).

Inner shaft assembly 104 extends within lumen 112 of sheath 102. Proximal inner shaft 114 of inner shaft assembly 104 extends proximally through lumen 159 of adjustment device 150, continuing proximally through housing 182, and is rigidly connected to handle 180 such that lumen 122 provides access for auxiliary components (e.g., a guide wire) therein. Proximal inner shaft 114 may be coupled to handle 180, for example, and not by way of limitation, by adhesives, welding, clamping, and other coupling devices as appropriate. Inner shaft assembly 104 is fixed relative to handle 180.

Delivery sheath assembly 102 extends within passageway 128 of outer stability shaft 110. Shaft 118 of delivery sheath assembly 102 extends proximally through lumen 159 of adjustment device 150, continuing proximally into housing 182 of handle 180, and is rigidly connected to actuator mechanism 184 of handle 180. Shaft 118 may be coupled to actuator mechanism 184 by adhesives, welding, clamping, and other coupling devices as appropriate. Delivery sheath assembly 102 is movable relative to handle 180 and adjustment device 150 by actuator mechanism 184. However, if actuator mechanism 184 is not moved and handle 180 is moved, delivery sheath assembly 102 moves with handle 180, not relative to handle 180, as explained in more detail below.

Outer stability shaft 110 is disposed within distal portion of lumen 159 and is coupled to extension 160. For example, and not by way of limitation, outer stability shaft 110 may be coupled to extension 160 by adhesives, welding, clamping, and other coupling devices as appropriate. Although outer stability shaft 110 is described as being attached to extension 160, outer stability shaft 110 may be coupled to housing 151 of adjustment device 150, and extension 160 may be excluded. Outer stability shaft 110 extends distally from adjustment device 150, and encompasses a portion of the length of shaft 118, thus stabilizing at least a portion of shaft 118 without impeding sliding/transitioning of capsule 108 from the delivery configuration to the deployed configuration. Outer stability shaft 110 is fixed longitudinally relative to adjustment device 150.

With the above understanding of components in mind, operation and interaction of components of the present disclosure may be explained. FIG. 4 illustrates adjustment device 150. Adjustment mechanism 152 of adjustment device 150 is configured such that, as first toothed wheel 154 is rotated in a first direction, teeth 153 on first toothed wheel 154 engage with teeth 156 on second toothed wheel 158 such that rotation of first toothed wheel 154 causes rotation of second toothed wheel 158 in a second direction opposite the first direction. Teeth 156 of second toothed wheel 158 engage teeth 188 on handle extension 186 such that handle extension 186, and thus handle 180, moves relative to housing 151 of adjustment device 150. Inner shaft assembly 104 and delivery sheath assembly 102, being coupled to handle 180, also move relative to housing 151 of adjustment device 150. The engagement of teeth 156 on second toothed wheel 158 with teeth 188 on handle extension 186 also translates the rotational movement of second toothed wheel 158 to longitudinal movement of handle extension 186.

Handle 180 resides partially within the proximal end of adjustment lumen 159 of adjustment housing 151 such that teeth 188 on handle extension 186 are oriented parallel to longitudinal axis LA of adjustment device 150. First toothed wheel 154 and second toothed wheel 158 are oriented relative to longitudinal axis LA such that rotation of first toothed wheel 154 is parallel to longitudinal axis LA (i.e., first pivot axis 155 is transverse to longitudinal axis LA). In the embodiment shown, second toothed wheel 158 is also oriented relative to longitudinal axis LA such that rotation of second toothed wheel 158 is parallel to longitudinal axis LA (i.e., second pivot axis 157 is transverse to longitudinal axis LA). Adjustment mechanism 154 is configured to selectively move handle 180, delivery sheath assembly 102, and inner shaft assembly 104 relative to housing 151 of adjustment device 150 and outer stability shaft 110 a distance in the range of 1-50 mm, preferably in the range of 10-40 mm, and most preferably in the range of 20-30 mm, up to 25.0 mm.

FIGS. 7A-7E schematically show delivery device 100 in operation. In FIGS. 7A-7E the exposed portion of first toothed wheel 154 is rotated in a first direction 200, towards the distal end of adjustment device 150. Adjustment mechanism 152 is configured such that, as toothed wheel 154 is rotated in first direction 200, teeth 153 on first toothed wheel 154 engage teeth 156 on second toothed wheel 158 to rotate second toothed wheel 158 in direction 202. Teeth 156 of second toothed wheel 158 engage teeth 188 on handle extension 186 such that handle extension 186, and thus handle 180, move in distal direction 204, while housing 151 of adjustment device 150 remains stationary. Delivery sheath assembly 102 and inner shaft assembly 104, being coupled to handle 180, also move in distal direction 204. Although FIGS. 7A-7E only show movement of first toothed wheel 154 in first direction 200, resulting movement of handle 180, inner shaft assembly 104, and delivery sheath assembly 102 in distal direction 204, movement of first toothed wheel 154 in second direction 202 results in movement of second toothed wheel 158 in first direction 200, and movement of handle 180, inner shaft assembly 104, and delivery sheath assembly 102 in a proximal direction opposite distal direction 204. Movement direction, either distally or proximally, of handle 180, delivery sheath assembly 102, and inner shaft assembly 104, relative to housing 151 of adjustment device 150 is dependent upon the direction of rotation of first toothed wheel 154. Rotational direction of first toothed wheel 154 is selected by operator manipulation.

Figure 8A:
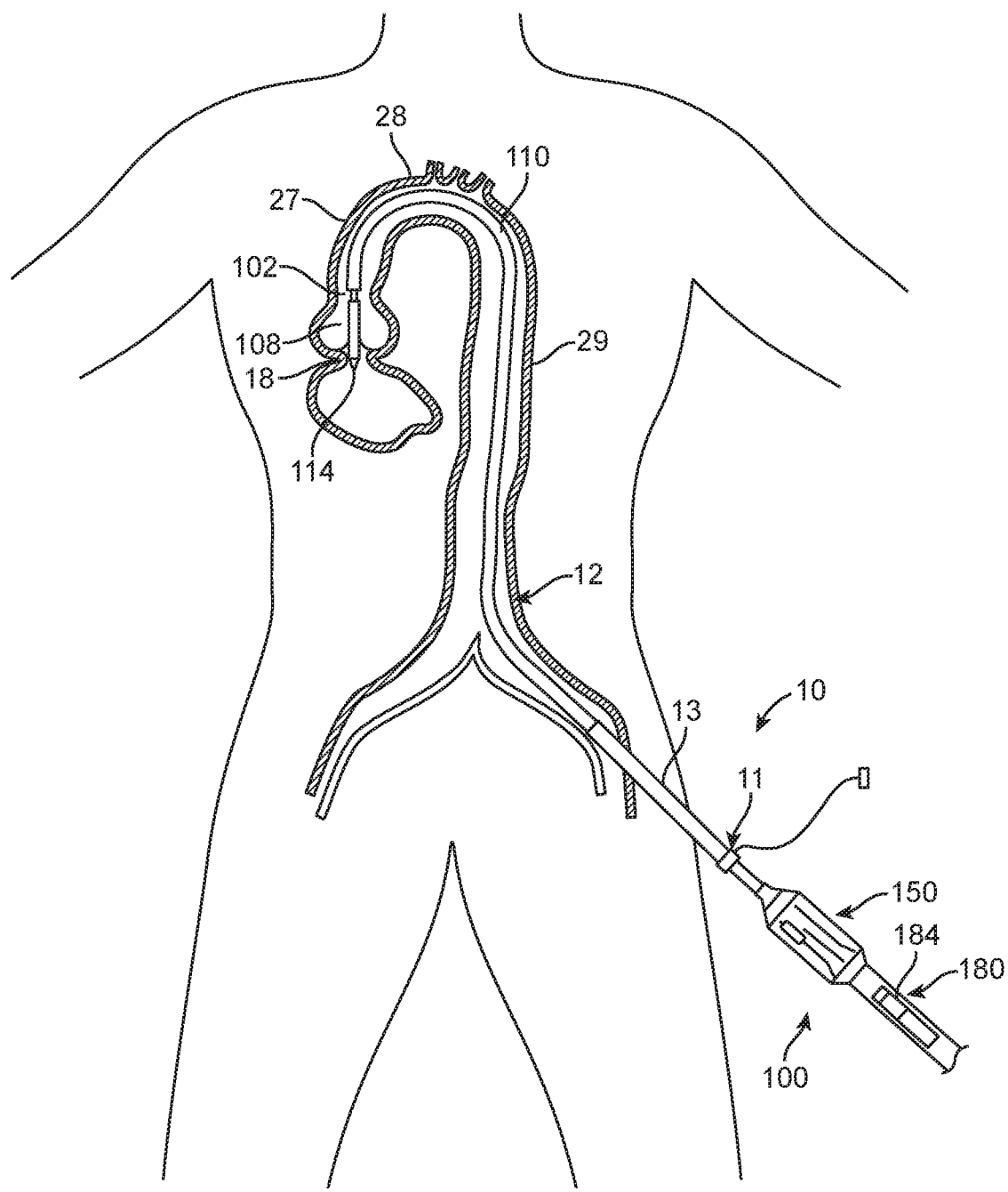
FIGS. 8A-8B are simplified illustrations of a method of adjusting the location of a stented prosthetic heart valve during transcatheter delivery using the delivery device of FIG. 3.
Figure 8B:
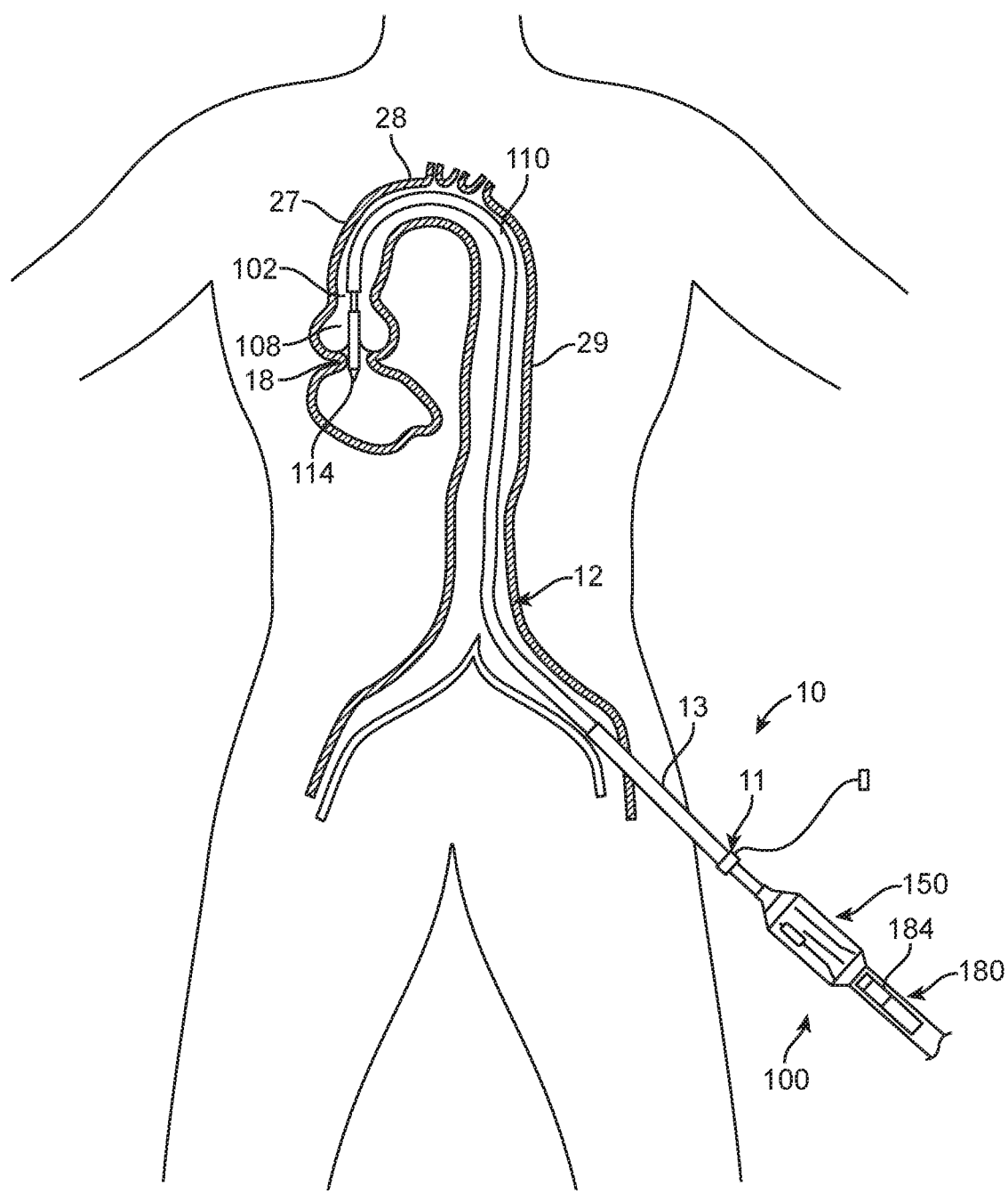

In some embodiments, delivery device 100 can be used in conjunction with an introducer device 10 as shown in FIGS. 8A-8B. Introducer devices generally include an introducer sheath 13 and a valve 11. The introducer sheath 13 is typically a resilient body. To access a bodily lumen (e.g., femoral artery) of the patient, an incision is formed in the patient's skin, and introducer sheath 13 inserted through the incision and into the desired bodily lumen. Valve 11 fluidly closes the connection with the bodily lumen external the patient. Delivery device 100 is then inserted into the bodily lumen via introducer device 10.

As generally reflected in FIG. 8A, introducer sheath 13 has an inner diameter greater than outer stability shaft 110 (as well as capsule 108), such that capsule 108 can readily be delivered through the bodily lumen, directed to other branches of the patient's vasculature 12, and then into the defective heart valve implantation site 18 (e.g., aortic heart valve). In this regard, introducer valve 11 frictionally contacts outer stability shaft 110, thereby establishing a low friction hemostasis seal around outer stability shaft 110. Outer stability shaft 110 isolates delivery sheath assembly 102 from introducer sheath 13 and valve 11. While outer stability shaft 110 is in physical contact with portions of introducer device 10, the delivery sheath assembly 102 does not directly contact introducer device 10. Further, outer stability shaft 110 overtly supports shaft 118 in traversing the tortuous vasculature, minimizing occurrences of kinks forming in shaft 118 when, for example, moving across the aortic arch 28.

Figure 1A:
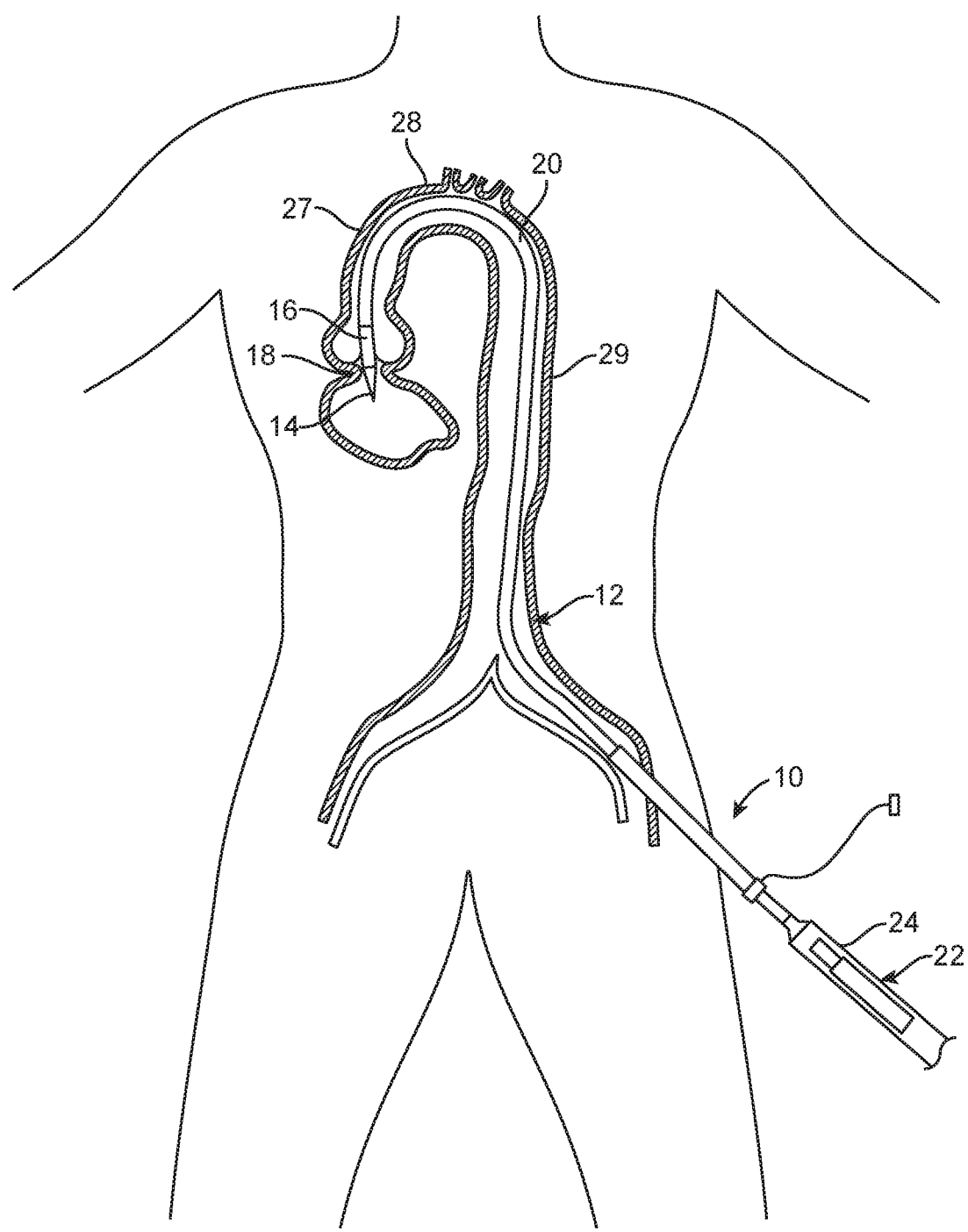
FIGS. 1A-1B are simplified illustrations of conventional transcatheter delivery of a stented prosthetic heart valve.
Figure 1B:
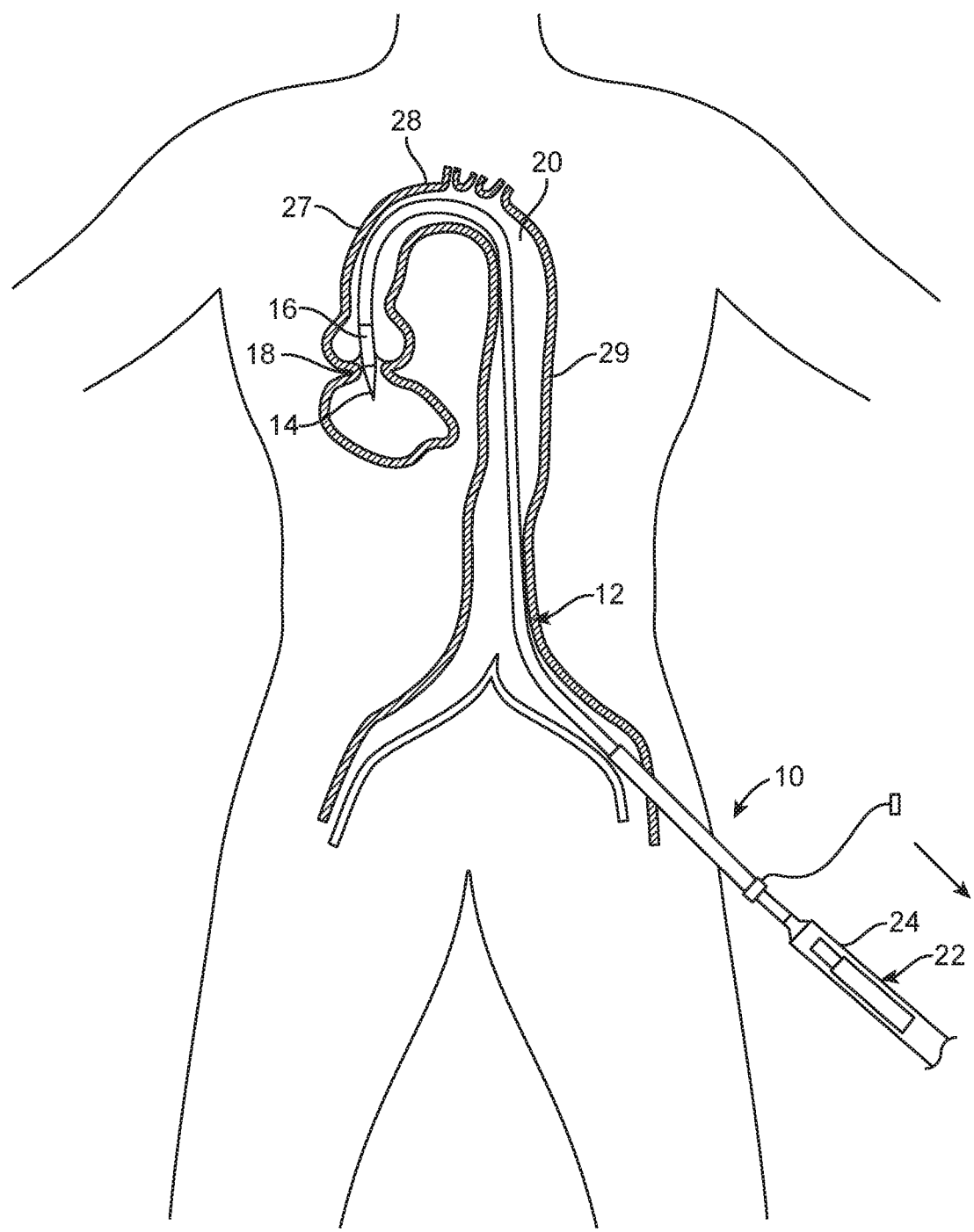

Once the prosthetic heart valve 30 is positioned near the deployment site, as shown in FIG. 8A, the position of capsule 108 and retention member 120 may be finely adjusted to the desired location within the native heart valve 18 via user manipulation of adjustment mechanism 152. Because outer stability shaft 110 is not moved when adjustment mechanism 152 is manipulated, outer stability shaft 110 does not move within the aorta as described with respect to FIGS. 1A and 1B. Thus, movement of handle 180 by adjustment mechanism 152 is directly translated to movement of capsule 108 and retention member 120, with the prosthetic heart valve disposed within capsule 108. Determination of optimal deployment location is based upon known methods such as, but not limited to sonography and radioopaque markers. As shown in FIG. 8A, capsule 108 has been roughly positioned proximally of native aortic valve 18, but is not in the desired implantation location.

Thus, a user interface for adjustment mechanism 152 of adjustment device 150 is manipulated by the user to manipulate capsule 108 to the desired deployment location. For the delivery device of the embodiment of FIG. 7, first toothed wheel 154 of adjustment mechanism 152 is rotated in direction 200, towards the distal end of adjustment device 150, such that handle 180, delivery sheath assembly 102 (including capsule 108), and inner shaft assembly 104 advance incrementally towards the desired deployment location, as shown in FIG. 8B. The movement of handle 180, delivery sheath assembly 102 (including capsule 108), and inner shaft assembly 104 is relative to adjustment device 150 and outer stability shaft 110, as described above.

To deploy prosthetic heart valve 16 from delivery device 100 at the desired deployment location, actuator mechanism 184 of handle 180 is operated proximally to retract delivery sheath assembly 102. In particular, shaft 118 and capsule 108 are moved proximally to withdraw capsule 108 from its position surrounding prosthetic heart valve 30, thereby permitting prosthetic heart valve 30 to self-deploy from delivery device 100.

While only some embodiments have been described herein, it should be understood that it has been presented by way of illustration and example only, and not limitation. Various changes in form and detail can be made therein without departing from the spirit and scope of the invention, and each feature of the embodiment discussed herein, and of each reference cited herein, can be used in combination with the features of any other embodiment. All patents and publications discussed herein are incorporated by reference herein in their entirety.

What is claimed is:

1. A delivery device for percutaneously delivering a stented prosthetic heart valve, the stented prosthetic heart valve being radially expandable from a radially compressed configuration to a radially expanded configuration, the delivery device comprising:
   a sheath defining a lumen, wherein the sheath is configured to compressively constrain the stented prosthetic heart valve;
   a handle including a handle housing and an actuator, wherein the sheath is at least partially disposed within the handle housing, and wherein the actuator is coupled to a proximal portion of the sheath and is configured to selectively move the sheath relative to the handle housing to release the stented prosthetic heart valve;
   an adjustment device coupled to the handle, wherein the adjustment device includes an adjustment lumen through which the sheath and at least a portion of the handle slidably extend, wherein the adjustment device includes a fine adjustment mechanism; and
   an outer stability shaft coupled to the adjustment device, wherein the fine adjustment mechanism is configured to selectively move the handle housing and the sheath relative to the adjustment device and the outer stability shaft.

2. The delivery device of claim 1, wherein the fine adjustment mechanism includes a toothed wheel that is coupled to teeth on the handle.

3. The delivery device of claim 2, wherein the toothed wheel is oriented relative to a longitudinal axis of the adjustment device and the handle such that the toothed wheel rotates parallel to the longitudinal axis to move the handle and the sheath.

4. The delivery device of claim 2, further comprising a second toothed wheel disposed between the toothed wheel and the teeth on the handle, wherein the toothed wheel is coupled to the second toothed wheel and the second toothed wheel is coupled to the teeth on the handle.

5. The delivery device of claim 1, wherein the outer stability shaft is configured to isolate the sheath from a separate introducer valve component through which the delivery device is inserted into a patient.

6. The delivery device of claim 1, wherein the sheath comprises a distal capsule and a proximal shaft, wherein the proximal shaft is attached to the actuator of the handle, and wherein the distal capsule is configured to compressively constrain the stented prosthetic heart valve.

7. The delivery device of claim 6, wherein an outer diameter of the capsule is greater than an outer diameter of the proximal shaft, the proximal shaft being affixed to the capsule at a connection point, and further wherein in a delivery configuration, the connection point is distal of the distal end of the stability shaft by a distance in the range of 3-13 cm.

8. The delivery device of claim 6, wherein an outer diameter of the capsule is greater than an outer diameter of the proximal shaft, the capsule being affixed to the proximal shaft at a connection point, and further wherein in a deployed configuration, the connection point is distal of the distal end of the stability shaft.

9. The delivery device of claim 1, wherein the adjustment mechanism is configured to selectively move the handle and the sheath relative to the adjustment device and the outer stability shaft a distance in the range of 10-40 mm.

10. The delivery device of claim 1, wherein the handle further includes a handle extension extending distally from a distal end of the handle housing, wherein the handle extension extends into the adjustment lumen.

11. The delivery device of claim 10, wherein the fine adjustment mechanism includes a toothed wheel that is coupled to teeth on the handle extension.

12. The delivery device of claim 11, wherein the toothed wheel is oriented relative to a longitudinal axis of the adjustment device and the handle such that the toothed wheel rotates parallel to the longitudinal axis to move the handle and the sheath.

13. The delivery device of claim 11, further comprising a second toothed wheel disposed between the toothed wheel and the teeth on the handle extension, wherein the toothed wheel is coupled to the second toothed wheel and the second toothed wheel is coupled to the teeth on the handle extension.

* * * * *